United States Patent [19]

Schaaf et al.

[11] 3,992,439
[45] Nov. 16, 1976

[54] SYNTHESIS OF PROSTAGLANDINS OF THE "ONE"-SERIES

[75] Inventors: Thomas K. Schaaf, Old Lyme, Conn.; Elias J. Corey, Cambridge, Mass.

[73] Assignee: Pfizer Inc., New York, N.Y.

[22] Filed: Feb. 14, 1975

[21] Appl. No.: 549,875

Related U.S. Application Data

[62] Division of Ser. No. 244,882, April 17, 1972, Pat. No. 3,887,587.

[52] U.S. Cl. .......................... 260/514 D; 260/468 D
[51] Int. Cl.² ......................................... C07C 177/00
[58] Field of Search ..................... 260/514 D, 468 D

[56] References Cited
UNITED STATES PATENTS

3,867,460   2/1975   Corey .............................. 260/606.5

OTHER PUBLICATIONS

Doria et al., Tet. Letters, 4307, (1972).
Corey et al., I, JACS, 91, 5675, (1969).
Corey et al., II, JACS, 92, 397, (1970).
Corey et al., III, JACS, 92, 2586, (1970).
Corey et al., IV, JACS, 93, 1490, (1971).

*Primary Examiner*—Robert Gerstl
*Attorney, Agent, or Firm*—Connolly and Hutz

[57] ABSTRACT

In the synthesis of prostaglandins of the "one"-series an alteration in the conventional reaction sequence avoids side reactions and provides an improved synthesis via a series of novel intermediates. In this improved synthesis the side chain at the 8 position is attached to the five membered ring before the side chain at the 12 position is attached.

2 Claims, No Drawings

SYNTHESIS OF PROSTAGLANDINS OF THE "ONE"-SERIES

CROSS REFERENCE TO RELATED APPLICATION

This application is a division of application Ser. No. 244,882, filed Apr. 17, 1972, now U.S. Pat. No. 3,887,587.

BACKGROUND OF THE INVENTION

This invention relates to the synthesis of prostaglandins of the "one"-series. In particular it relates to a process of catalytic reduction where by the ease of preparation of said prostaglandins is greatly enhanced. The pharmaceutical uses of prostaglandins of the "one"-series in fertility control, bronchodilation, and blood pressure regulation is well known.

The recent synthesis of prostaglandin $E_1$ in its optically active form constituted a notable achievement by E. J. Corey and his associates (J. Amer. Chem. Soc. 92, 2586 (1970); and references cited therein for other syntheses). This synthetic sequence is characterized by generally high-yield, stereocontrolled reactions. The selective reduction of the 11,15-bis-tetrahydropyranyl ether of prostaglandin $F_{2\alpha}$, an essential step in the Corey synthesis, is, however, a notable exception as it is exceedingly sensitive to reaction conditions, capricious, and as it is not amenable to large-scale preparation. The improved synthesis presented herein obviates this troublesome step and thereby greatly enhances the synthesis of the prostaglandins of the "one"-series.

SUMMARY OF THE INVENTION

The present invention comprises the improved step in the synthesis of prostaglandins of the "one"-series comprising catalytic hydrogenation of an unsaturated compound of the formula:

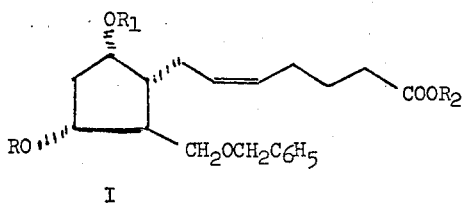

I to form a saturated compound of the formula:

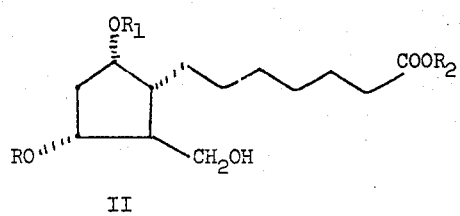

II wherein
- R is an organic protecting group stable to hydrogenation and to basic hydrolysis and easily removable by mild acid hydrolysis;
- $R_1$ is a hydrocarbyl carbonyl protecting group stable to hydrogenation and to acid hydrolysis and easily removable by mild basic hydrolysis; and
- $R_2$ is a hydrocarbyl protecting group stable to hydrogenation and to acid hydrolysis and easily removable by mild basic hydrolysis.

The invention further embraces the process wherein said unsaturated compound is prepared by contacting (4-carboxy-n-butyl)triphenyl phosphonium bromide with a compound of the formula:

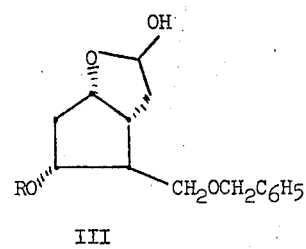

III to produce a hydroxycarboxylic acid of the formula:

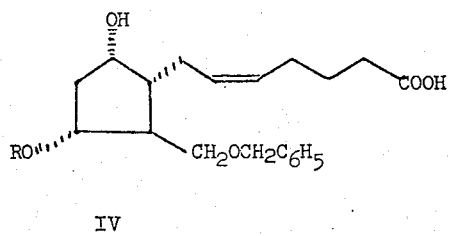

IV and acylating the hydroxy and esterifying the carboxy group of said hydroxycarboxylic acid wherein R is an organic protecting group stable to hydrogenation and to basic hydrolysis and easily removable by mild acid hydrolysis.

This invention also includes the process wherein said saturated compound is oxidized to an aldehyde of the formula:

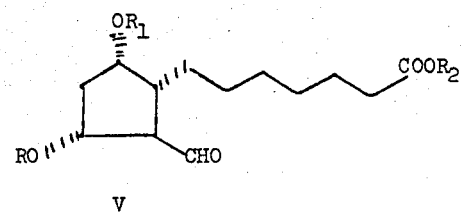

V said aldehyde is contacted with dimethyl-2-oxoheptyl-phosphonate to form a compound of the formula:

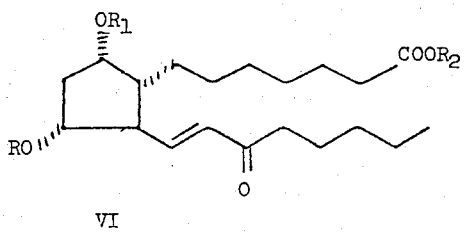

VI and said compound is reduced to a compound of the formula:

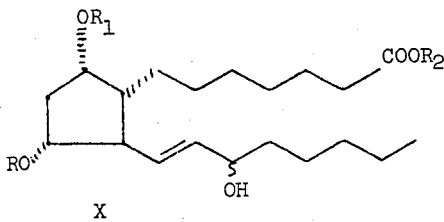

X wherein
R is an organic protecting group stable to hydrogenation and to basic hydrolysis and easily removable by mild acid hydrolysis;
$R_1$ is a hydrocarbyl carbonyl protecting group stable to hydrogenation and to acid hydrolysis and easily removable by mild basic hydrolysis; and
$R_2$ is a hydrocarbyl protecting group stable to hydrogenation and to acid hydrolysis and easily removable by mild basic hydrolysis.

In addition, Compounds I through X represent novel classes of valuable intermediates which constitute a further feature of the invention.

Preferred in the foregoing process is the case where I is represented by the formula:

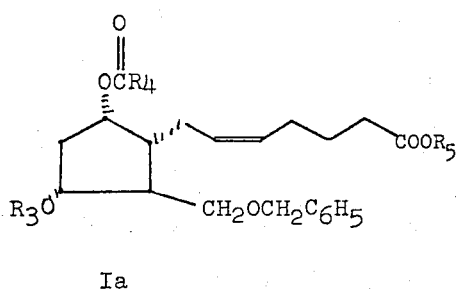

Ia wherein
$R_3$ is tetrahydropyranyl, tetrahydrofuranyl, or dimethylisopropylsilyl; and
$R_4$ and $R_5$ are each alkyl of from 1 to 8 carbon atoms, phenylalkyl having up to three carbon atoms in the alkyl moiety, phenyl, tolyl, biphenyl, or fluorenyl, and especially preferred is methyl 7-[2β-benzyloxymethyl-3α-(tetrahydropyran-2-yloxy)-5α-acetoxycyclopent-1α-yl]-cis-5-heptenoate.

Preferred in the above process is the instance wherein II is represented by the formula:

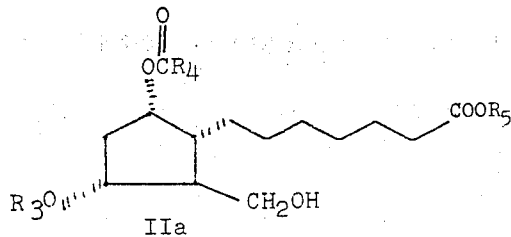

IIa wherein
$R_3$ is tetrahydropyranyl, tetrahydrofuranyl, or dimethylisopropylsilyl; and
$R_4$ and $R_5$ are each alkyl of from 1 to 8 carbon atoms, phenylalkyl having up to three carbon atoms in the alkyl moiety, phenyl, tolyl, biphenyl, or fluorenyl, and especially preferred is methyl 7-[2β-hydroxymethyl-3α-(tetrahydropyran-2-yloxy)-5α-acetoxycyclopent-1α-yl]heptanoate.

Also preferred in the above process is the case where III is represented by the formula:

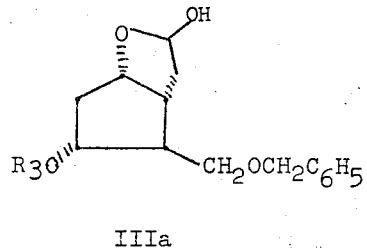

IIIa wherein
$R_3$ is tetrahydropyranyl, tetrahydrofuranyl, or dimethylisopropylsilyl, and especially preferred is 2-[2β-benzyloxymethyl-3α-(tetrahydropyran-2-yloxy)-5α-hydroxycyclopent-1α-yl]acetaldehyde, γ-hemiacetal.

Furthermore, the case is preferred where IV is represented by the formula:

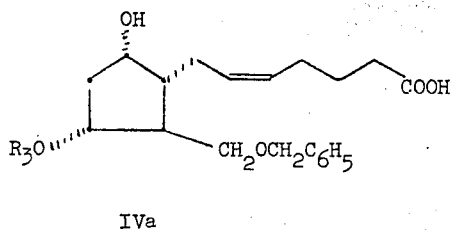

IVa wherein $R_3$ is tetrahydropyranyl, tetrahydrofuranyl, or dimethylisopropylsilyl, and especially preferred is 7-[2β-benzyloxymethyl-3α-tetrahydropyran-2-yloxy)-5α-hydroxycyclopent-1α-yl]-cis-5-heptenoic acid.

Also preferred is the instance where V is represented by the formula:

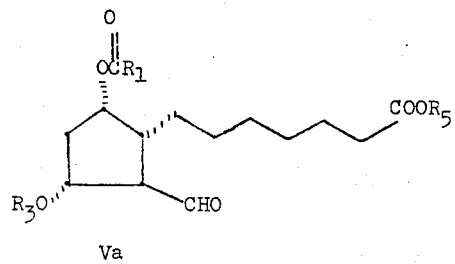

Va wherein
R₃ is tetrahydropyranyl, tetrahydrofuranyl, or dimethylisopropylsilyl; and
R₄ and R₅ are each alkyl of from 1 to 8 carbon atoms, phenylalkyl having up to three carbon atoms in the alkyl moiety, phenyl, tolyl, biphenyl, or fluorenyl, nd especially preferred is methyl 7-[2β-formyl-3α-tetrahydropyran-2-yloxy)-5α-acetoxycyclopent-1α-yl]heptanoate.

Also preferred is the case where VI is represented by the formula:

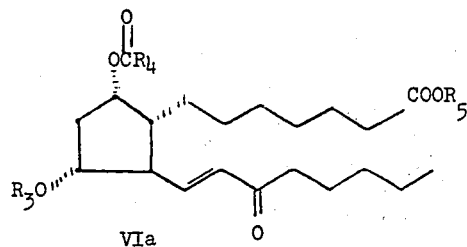

VIa wherein
R₃ is tetrahydropyranyl, tetrahydrofuranyl, or dimethylisopropylsilyl; and
R₄ and R₅ are each alkyl of from 1 to 8 cabon atoms, phenylalkyl having up to three carbon atoms in the alkyl moiety, phenyl, tolyl, biphenyl, or fluorenyl, and especially preferred is methyl 9α-acetoxy-11α-(tetrahydropyran-2-yloxy)-15-oxo-rans-13-prostenoate.

Also preferred is the case where X is represented by the formula:

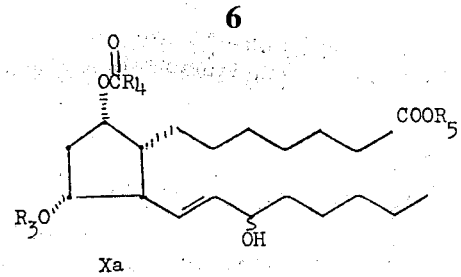

Xa wherein
R₃ is tetrahydropyranyl, tetrahydrofuranyl, or dimethylisopropylsilyl; and
R₄ and R₅ are each alkyl of from 1 to 8 carbon atoms, phenylalkyl having up to three carbon atoms in the alkyl moiety, phenyl, tolyl, biphenyl, or fluorenyl; and
especially preferred is methyl 9α-acetoxy-11α-(tetrahydropyran-2-yloxy)-15-hydroxy-trans-13-prostenoate.

DETAILED DESCRIPTION OF THE INVENTION

The present improvement in the synthesis of prostaglandins of the "one"-series can best be illustrated by means of a flo-sheet such as the one shown below in which the inventive step of primary interest is shown at I nd II. Processes leading up to this primary step are shown at VII through IX and III through IVb. Processes leading on from the primary step to prostaglandins of the "one"-series are shown at V and VI and X through XVIII.

Novel compounds are employed in various steps of this improved synthesis. For example, the compounds employed in steps I through VI and steps III through IVb are all novel.

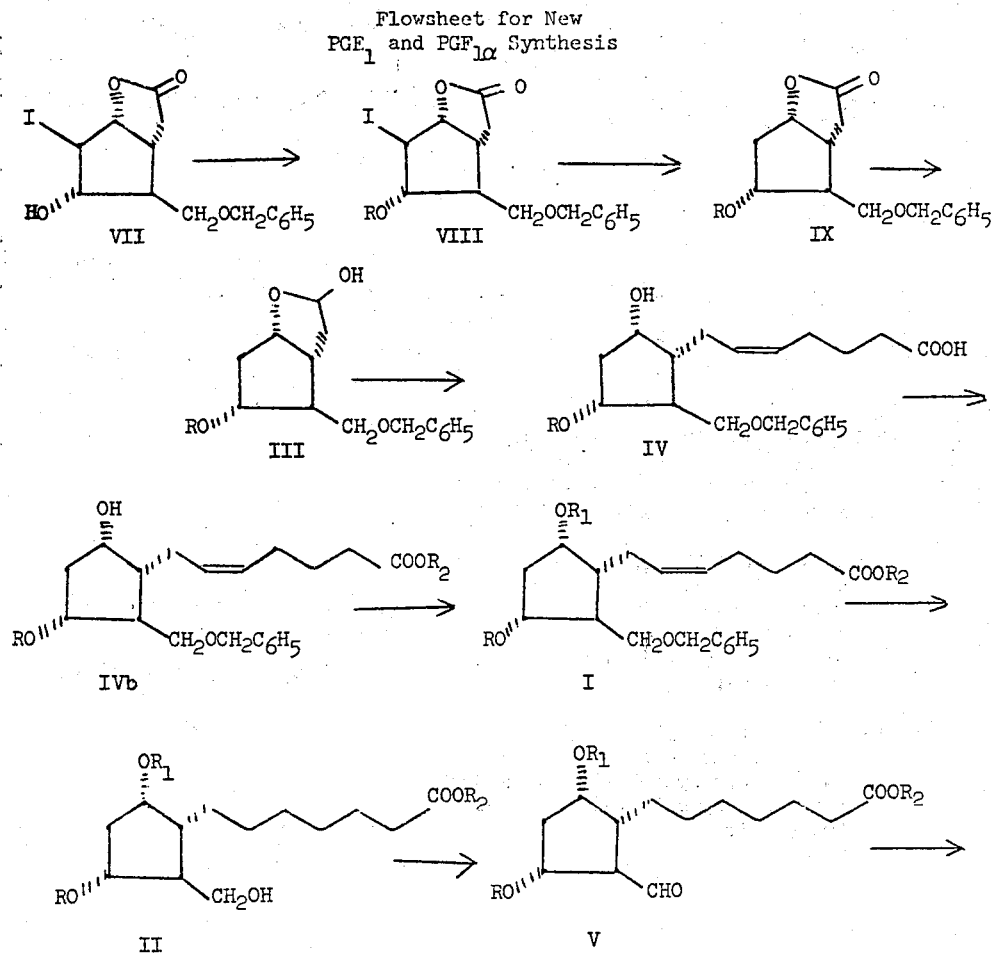

Flowsheet for New PGE₁ and PGF₁α Synthesis

Flowsheet for New PGE$_1$ and PGF$_{1\alpha}$ Synthesis -continued

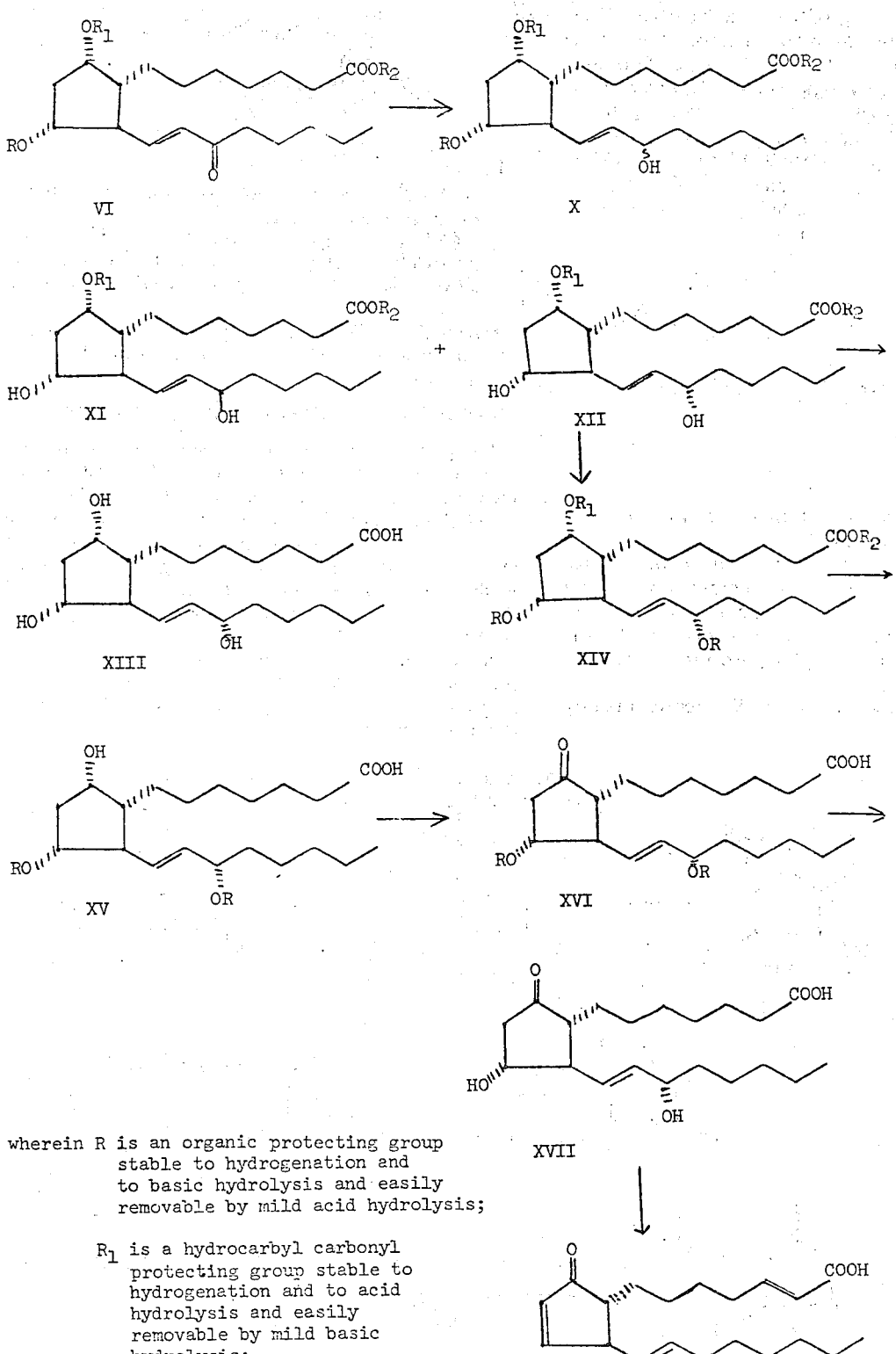

wherein R is an organic protecting group stable to hydrogenation and to basic hydrolysis and easily removable by mild acid hydrolysis;

R$_1$ is a hydrocarbyl carbonyl protecting group stable to hydrogenation and to acid hydrolysis and easily removable by mild basic hydrolysis;

and R$_2$ is a hydrocarbyl protecting group stable to hydrogenation and to acid hydrolysis and easily removable by mild basic hydrolysis.

A great many protecting groups for alcohols and caboxylic acids, as employed in the foregoing synthesis, are known to those skilled in the art. See for example: C. D. Dierassi, ed., "Steroid Reactions: An Outline for Organic Chemists", Holden-Day, San Francisco, 1963 pp 1-89; L. F. Fieser and M. Fieser, "Reagents for Organic Synthesis", John Wiley and Sons, Inc., New York, 1968; L. F. Fieser and M. Fieser, "Reagents for Organic Synthesis, Volume II", Wiley-Intersuence, New York, 1969. Protecting groups for alcohols stable to hydrogenation and to basic hydrolysis and easily removable by mild acid hydrolysis include, for example, tetrahydropyranyl, tetrahydrofuranyl, and dimethylisopropylsilyl. Likewise, hydrocarbyl carbonyl protecting groups for alcohols stable to hydrogenation and to acid hydrolysis and easily removable by mild basic hydrolysis include such radicals as alkanoyl of from 2 to 9 carbon atoms, phenyl alkanoyl having up to four carbon atoms in the alkanoyl moiety, phenyl carbonyl, tolyl carbonyl, biphenyl carbonyl, and fluorenyl carbonyl.

Further, hydrocarbyl protecting groups for caboxylic acids stable to hydrogenation and to acid hydrolysis and easily removable by mild basic hydrolysis include such radicals as alkyl of 1 to 8 carbon atoms, phenyl alkyl having up to 3 carbon atoms in the alkyl moiety, phenyl, tolyl, biphenyl, and fluorenyl. A number of equivalent blocking groups will occur to those skilled in the art.

The starting compound for the process of this invention (VII) is prepared by known methods [Corey, et al. J. Amer. Chem. Soc. 92, 1490 (1971)] by iodolactonization of a known (+)-amphetamine salt. VII is then converted to VIII, which is then deiodinated to IX.

To prepare III, the first novel compound encountered in the synthetic sequence presented above, the ether lactone IX in toluene is mixed with diisobutylaluminum hydride in hexane. The reaction mixture is quenched, diluted with ether, washed with sodium potassium tartrate and brine, and dried and concentrated to hemiacetal III.

Hemiacetal III is combined with the ylide solution produced from (4-carboxy-n-butyl)triphenylphosphonium bromide and sodium methylsulfinylmethide in dimethyl sulfoxide. The basic solution thus produced is extracted with ethyl acetate:ether, acidified, further extracted, washed, dried and concentrated. The crude yellow oil is purified by chromatography to the acid IV.

Acid IV in anhydrous ether titrated with an ethereal diazoalkane such as diazomethane or a diazo-aromatic hydrocarbon, and the ethereal solution thus produced is then washed in base and brine, dried, and concentrated to the hydroxyester IVb.

Hydroxyester IVb in pyridine is combined with either acetic anhydride, other carboxylic acid anhydrides or caboxylic acid chlorides. The ethereal solution thus produced is washed, dried, and concentrated to form the carbohydroxyester I.

The carbohydroxy ester I is catalytically reduced, for example, with palladium on carbon in ethanol:acetic acid under a hydrogen atmosphere. The mixture is filtered and concentrated to the alcohol II.

Alcohol II is combined with a solution obtained by reacting pyridine in methylene chloride with chromium trioxide. The suspension formed is stirred with sodium bisulfate monohydrate and magnesium sulfate and is then filtered, washed, and concentrate to aldehyde V.

Aldehyde V is combined with a suspension of sodium hydride in mineral oil in dimethoxyethane to which has been added dimethyl-2-oxoheptylphosphonate. The reaction mixture is stirred under nitrogen and is then quenched with acid. The semisolid product is filtered and concentrated and then may be purified by chromatography to the enone VI.

Enone VI may be reduced to the epimeric mixture X with, for example, zinc borohydride. Compound X may be converted to a novel compound of the formula:

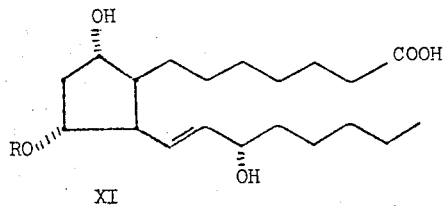

XI wherein
R is an organic protecting group stable to hydrogenation and to basic hydrolysis and easily removable by mild acid hydrolysis by treatment with base and aqueous tetrahydrofuran in a solvent such as methanol. The desired product may be purified by column chromatography.

A preferred form of this compound is represented by the formula:

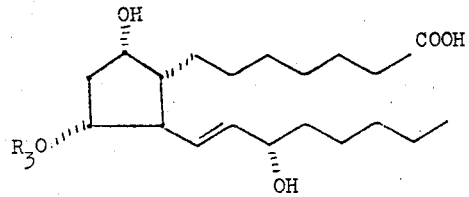

wherein $R_3$ is tetrahydropyranyl, tetrahydrofuranyl, or dimethylisopropylsilyl. Especially preferred is 9α-15α-dihydroxy-11α-(tetrahydropyran-2-yloxy)-trans-13-prostenoic acid.

In accordance with the process of the present invention, carbohydroxy ester I may be suspended in any of a variety of reaction inert solvent media in the presence of a catalytic amount of a noble metal catalyst and contacted with hydrogen at an appropriate temperature and pressure until reduction occurs. Thereafter, the desired alcohol II may be recovered by conventional procedure involving catalyst removal and recovery from the solvent medium.

As used herein "reaction inert solvent medium" refers to any medium which is a solvent or suitable suspending agent for the reactant, is stable under the hydrogenation conditions and does not interfere with the effectiveness of the catalyst or interact with the reactant or product. Polar organic solvents are generally suitable and include the lower alkanols such as methanol, ethanol, and butanol, etc., cyclic and straight chain water soluble ethers such as dioxane, tetrahydrofuran, diethylene glycol monomethylether, 2-ethoxyethanol, the lower alkanoic acids such as acetic acid, propionic acid, aqueous media including the foregoing solvents, dilute aqueous hydrochloric acid, etc. As will be appreciated, these solvents and others are conventional in known hydrogenation techniques and hence are not critical. Preferred solvent usage is illustrated in the working examples appearing hereinafter.

The temperature is no more critical in the present process than it is in other known hydrogenations. Thus, the preferred temperature range is from about 0° to about 60° C., the preferred temperature within this range being from about 10°–50° C. and preferably room temperature. At temperatures below 0° C. the reaction is inordinately slow whereas at temperatures above about 60° C., decomposition of the starting material may occur. As is to be expected, the higher the temperature, the faster the reaction rate.

The noble metal catalysts as employed in the present invention include platinum, palladium, rhenium, rhodium and ruthenium, either of the supported or non-supported type, as well as the known catalytic compounds thereof such as the oxides, chlorides, etc. Examples of suitable catalyst supports include carbon, silica and barium sulfate. The catalysts may be preformed or formed in situ by prereduction of an appropriate salt of the catalytic compound. Examples of preferred catalysts are 5% palladium-on-carbon, 5% platinum-on-carbon, 5% rhodium-on-carbon, platinum chloride, palladium chloride, platinum oxide and ruthenium oxide. Materials such as the latter, where the metal is in a combined, non-elemental form, generally require prereduction before the hydrogenation can take place. This is accomplished simply by suspending the catalyst precursor in the hydrogenation medium, hydrogenating it, adding the substrate and continuing the hydrogenation. Alternatively, all of the components can be incorporated at once and hydrogenation commenced. The former procedure has the advantage of permitting the operator to separately determine the quantity of hydrogen absorbed during the catalyst pre-reduction and hydrogenolysis phase. The extent of hydrogenation can then be more readily controlled.

The expression "catalytic amount" as used herein is well understood by those skilled in the art of hydrogenation, and is illustrated in the examples appearing herein.

The pressure employed during hydrogenation is not critical and is primarily dependent upon apparatus availability. In general, pressures of from atmospheric to 2,000 p.s.i. are preferred. As is known, hydrogenation at atmospheric pressure is generally carried out in equipment wherein a measured volume of hydrogen contained in a reservoir is attached to a manometer in order to measure the volume of hydrogen consumed. Alternatively, a citrate of magnesia bottle and mechanical shaker with a calibrated pressure gauge, or a high pressure autoclave of the stirred or shaken variety may be employed.

Likewise, in the other reaction steps described herein and in the appended claims, such as oxidation of an alcohol to form an aldehyde, the reaction conditions are not critical and a wide variety of appropriate, known techniques will occur to those skilled in the art. The invention claimed is not limited to the specific conditions cited in the examples to follow.

The remainder of the compounds employed in the present improved synthesis of prostaglandins of the "one"-series are not novel. Details of the remainder of the synthesis have been published by Corey and his co-workers (J. Amer. Chem. Soc. 91, 535 (1969), and can briefly be summarized as follows: Hydrolysis of the epimeric mixture X with acetic acid:water followed by purification by column chromatography afford the diols XI (eluted first) and XII (eluted last). The diol XII is converted into $PGF_{1\alpha}$ (XIII) by the action of aqueous methanolic sodium hydroxide.

The diol XII is also pyranylated with dihydropyran in methylene chloride to give the bis-tetrahydropyranyl ether XIV. Treatment of XIV with aqueous methanolic sodium hydroxide gives the alcohol XV. Oxidation of the alcohol XV with Jones' reagent followed by hydrolysis of the resulting ketone XVI will afford $PGE_1$ (XVII). To produce $PGA_1$ (XVIII), XVII is treated with 97% formic acid for 2–3 hours at room temperature (Corey et al., J. Amer. Chem. Soc. 90, 3245 (1968).

If 15-lower alkyl derivatives of the prostaglandins of the "one"-series are desired, they may be prepared by adding an alkyl lithium compound, such as methyllithium, to enone VI in ether, dropwise at −78° C. After quenching, the mixture is warmed to room temperature, washed in water, dried and concentrated to a 15-lower alkyl prostaglandin intermediate such as the 15-methyl derivative of X. The remainder of the synthesis of 15-lower alkyl derivatives of prostaglandins of the "one"-series is carried out as described above.

The following examples are illustrative and in no way limit the scope of the appended claims.

EXAMPLE I

To a solution, cooled to 5°, of 5.82 g. (150 mmoles) of the known iodoalcohol in 15 ml. of methylene chloride was added 1.71 ml. (18.7 mmoles) of dihydropyran and 27 mg. (0.15 mmole) of p-toluenesulfonic acid monohydrate. After 20 minutes the reaction was diluted with methylene chloride (30 ml.) and was washed with saturated sodium bicarbonate (5 ml.) and saturated brine (5 ml.), was dried (anhydrous magnesium sulfate) and was concentrated to afford the pale-yellow, oily 2-[2β-benzyloxymethyl-3α-(tetrahydropyran-2-yloxy)-5α-hydroxy-4β-iodocyclopent-1α-yl]acetic acid, γ-lactone weighing 6.76 g. (95.5% yield). The nmr, ir, and mass spectra were consonant with the assigned structure.

Spectra:

| ir (CHCl$_3$): | | | |
|---|---|---|---|
| 1780 cm$^{-1}$ | lactone carbonyl | | |
| nmr (CDCl$_3$): | | | |
| 7.33 δ | singlet | 5H | aromatic |
| 4.52 δ | singlet | 2H | φ—C$\underline{H}_2$—O— |
| 5.22–4.08 δ | multiplet | 4H | C$\underline{H}$—O & C$\underline{H}$-I |
| 3.62 δ | quartet | 2H | —C$\underline{H}_2$—O—Bz |
| | J = 6 cps | | |
| | J = 3 cps | | |
| 3.04–2.48 δ | multiplet | 6H | —C$\underline{H}_2$—C=O & —C$\underline{H}_2$—O |
| 1.80–1.30 δ | multiplet | 5H | remaining protons |

EXAMPLE II

A solution of 6.76 g. (14.3 moles) of the crude iodoether prepared in Example I, 5.22 ml. (17.9 mmoles) of tri-n-butyltin hydride and 71.5 ml. of benzene was stirred at 50° under nitrogen for 1.0 hour. The mixture was then cooled to room temperature and was vigorously washed with saturated sodium carbonate (3x), was dried (anhydrous magnesium sulfate), and was concentrated to afford a biphasal oil. The oil was purified by chromatography using firat a 1:1 mixture of benzene:ether then ether as eluents. After removal of high R$_f$ tin byproducts the desired 2-[2β-benzyloxymethyl-3α-(tetrahydropyran-2-yloxy)-5α-hydroxycyclopent-1α-yl]acetic acid, γ-lactone was eluted weighing 3.40 g. (68.7% yield). The structure of this oil was confirmed by its ir, nmr, and mass spectra.

Spectra:

| ir (CHCl$_3$) | | | |
|---|---|---|---|
| 1780 cm$^{-1}$ | | lactone carbonyl | |
| nmr (CDCl$_3$) | | | |
| 7.33 δ | singlet | 5H | aromatic |
| 4.49 δ | singlet | 2H | φ—C$\underline{H}_2$—O— |
| 3.99–5.13 δ | multiplet | 3H | —C$\underline{H}$—O |
| 3.41 δ | quartet | 2H | —C$\underline{H}_2$—O—BZ |
| | J = 6 cps | | |
| | J = 2 cps | | |
| 1.98–2.99 δ | multiplet | 6H | —C$\underline{H}_2$—O & —C$\underline{H}_2\overset{O}{\overset{\|}{C}}$— |
| 1.26–72 δ | multiplet | 7H | remaining protons |

EXAMPLE III

To a stirred solution, cooled to −78°, of the chromatographed ether lactone prepared in Example II in 78.8 ml. of toluene was added 13.4 ml. (10.8 mmoles) of a 0.805M solution of diisobutylaluminum hydride in hexane dropwise. The solution was stirred in the cold under nitrogen for 1.0 hour then was quenched by the dropwise addition of methanol until gas evolution ceased. The quenched mixture was warmed to room temperature, was diluted with ether (79 ml.), was washed with 50% sodium potassium tartrate (3×) and saturated brine (1×), was dried (anhydrous magnesium sulfate, and was concentrated to afford the crude, colorless, oily 2-[2$\beta$-benzyloxymethyl-3$\alpha$-(tetrahydropyran-2-yloxy)-5$\alpha$-hydroxycyclopent-1$\alpha$-yl]acetaldehyde, $\gamma$-hemiacetal weighing 3.15 g. (92.0% yield). The ir, nmr, and mass spectra of the oil were consistent with the assigned structure.

Spectra:

ir (CHCl$_3$):
no carbonyl
nmr (CDCl$_3$):

| | | | |
|---|---|---|---|
| 7.31 δ | singlet | 5H | aromatic |
| 5.32–5.75 δ | broad singlet | 1H | O$\underline{H}$ |
| 4.50 δ | singlet | 2H | $\phi$C$\underline{H}_2$—O |
| 4.45–4.98 δ | multiplet | 2H | O—C$\underline{H}$—O |
| 3.44 δ | quartet J = 9 cps J = 4 cps | 2H | —C$\underline{H}_2$O—BZ |
| 1.20–4.40 δ | multiplets | 16H | remaining protons |

EXAMPLE IV

To a solution of 4.96 g. (11.2 mmoles) of (4-carboxy-n-butyl)triphenylphosphonium bromide in 8.85 ml. of dimethyl sulfoxide was added dropwise 9.73 ml. (21.2 mmoles) of a 2.18 M solution of sodium methylsulfinylmethide in dimethyl sulfoxide. To the resultant red ylide solution was added dropwise over a period of 1.0 hour a solution of 1.57 g. (4.50 mmoles) of the crude hemiacetal prepared in Example III in 13.7 ml. of dimethyl sulfoxide. After being stirred for an additional 45 minutes the reaction was poured onto ice-water. The basic aqueous solution was extracted with a 2:1 mixture of ethyl acetate:ether (2 × 60 ml.), was then covered with ethyl acetate, and was acidified with 1.0 N hydrochloric acid to pH~3. The aqueous layer was extracted further with ethyl acetate; the combined ethyl acetate extracts were washed with water, were dried (anhydrous magnesium sulfate), and were concentrated to a viscous yellow oil. The crude oil was purified by chromatography on 30 g. of silica gel using ethyl acetate as eluent. After elution of high R$_f$ impurities the desired 7-[2$\beta$-benzyloxymethyl-3$\alpha$-(tetrahydropyran-2-yloxy)-5$\alpha$-hydroxycyclopent-1$\alpha$-yl]-cis-5-heptenoic acid was collected weighing 1.75 g. (90.0% yield).

Spectra:

ir (CHCl$_3$):
5.82 μ   acid   carbonyl
nmr (CDCl$_3$):

| | | | |
|---|---|---|---|
| 7.30 δ | singlet | 5H | aromatic |
| 6.44–7.00 δ | broad singlet | 2H | —OH |
| 5.28–5.58 δ | multiplet | 2H | olefinic |
| 4.62–4.79 δ | broad singlet | 1H | —O—C$\underline{H}$—O |
| 4.51 δ | singlet | 2H | $\phi$—C$\underline{H}_2$—O |
| 3.23–4.38 δ | multiplets | 8H | —C$\underline{H}_2$—O & —C$\underline{H}$—O |
| 1.22–2.53 δ | multiplets | 16H | remaining protons |

Optical Rotation:
[$\alpha$]$_D^{25}$ = +15.1° (C 9.94, HCCl$_3$).

EXAMPLE V

A solution of 1.75 g. (4.06 mmoles) of the chromatographed acid prepared in Example IV in 17.5 ml. of anhydrous ether was titrated at room temperature with an ethereal diazomethane solution until the yellow color persisted for 5 minutes. The reaction was then decolorized by the dropwise addition of glacial acetic acid. The ethereal solution was then washed with saturated sodium bicarbonate (1×) and saturated brine (1×), was dried (anhydrous magnesium sulfate), and was concentrated to afford the faintly-yellow, oily methyl 7-[2$\beta$-benzyloxymethyl-3$\alpha$-(tetrahydropyran-2-yloxy)-5$\alpha$-hydroxycyclopent-1$\alpha$-yl]-cis-5-heptenoate weighing 1.80 g. (99.0% yield).

Spectra:

ir (CHCl$_3$):
5.77 μ   Ester carbonyl
nmr (CDCl$_3$):

| | | | |
|---|---|---|---|
| 7.31 δ | singlet | 5H | aromatic |
| 5.62–5.30 δ | multiplet | 2H | olefinic |
| 4.81–4.63 δ | broad singlet | 1H | —O—C$\underline{H}$—O |
| 4.53 δ | singlet | 2H | $\phi$—C$\underline{H}_2$—O |
| 3.66 δ | singlet | 3H | —O—C$\underline{H}_3$ |
| 4.42–3.67 δ | multiplets | 9H | —C$\underline{H}_2$—O & —C$\underline{H}$—O |
| 2.55–1.36 δ | multiplets | 12H | remaining protons |

EXAMPLE VI

A mixture of 1.58 g. (3.54 mmoles) of the crude hydroxyester prepared in Example V, 5.0 ml. of pyridine and 0.736 ml. (7.78 mmoles) of acetic anhydride was stirred under nitrogen at 50° overnight. The mixture was then cooled to room temperature and was diluted with ether (75 ml.). The ethereal solution was washed with water (1×) and with saturated copper sulfate (3×), was dried (anhydrous magnesium sulfate), and was concentrated to afford the colorless, oily methyl 7-[2$\beta$-benzyloxymethyl-3$\alpha$-(tetrahydropyran-2-yloxy)-5$\alpha$-acetoxycyclopent-1$\alpha$-yl]-cis-5-heptenoate weighing 1.61 g. (93.5% yield).

Spectra:
ir (CHCl$_3$):
1750 cm$^{-1}$   ester carbonyls
nmr (CDCl$_3$):

| | | | |
|---|---|---|---|
| 7.30 δ | singlet | 5H | aromatic |
| 5.51–5.23 δ | multiplet | 2H | olefinic |
| 5.22–4.91 δ | multiplet | 1H | —C$\underline{H}$—O—Ac |
| 4.52 δ | singlet | 2H | $\phi$—C$\underline{H}_2$—O— |
| 3.63 δ | singlet | 3H | —O—C$\underline{H}_3$ |
| 4.67–3.20 δ | multiplets | 8H | —O—C$\underline{H}$— & —O—C$\underline{H}_2$— |
| 2.06 δ | singlet | 3H | $\overset{O}{\underset{\parallel}{-CCH_3}}$ |
| 2.55–1.22 δ | multiplets | 16H | remaining protons |

EXAMPLE VII

A heterogeneous mixture of 1.53 g. (3.14 mmoles) of the crude acetoxy ester prepared in Example VI, 305 mg. of 5% palladium on carbon, and 15.3 ml. of a 20:1 mixture of absolute ethanol:glacial acetic acid was stirred at room temperature under one atmosphere of hydrogen for 48 hours. The mixture was then filtered through Celite 545 and the filtrate was concentrated to afford the colorless, oily methyl 7-[2$\beta$-hydroxymethyl-3$\alpha$-(tetrahydropyran-2-yloxy)-5$\alpha$-acetoxycyclopent-1$\alpha$-yl]heptanoate weighing 1.10 g. (87.5% yield).

Spectra:
ir (CHCl$_3$):
1750 cm$^{-1}$   ester carbonyls
nmr (CDCl$_3$):

-continued

Spectra:

| | | | |
|---|---|---|---|
| 5.23–4.92 δ | multiplet | 1H | —CH—OAc |
| 4.83–4.46 δ | multiplet | 1H | —O—CH—O |
| 3.65 δ | singlet | 3H | —O—CH$_3$ |
| 4.32–3.18 δ | multiplets | 7H | —O—CH & —O—CH$_2$— |
| 3.06–2.70 δ | broad singlet | 1H | —OH |
| 2.04 δ | singlet | 3H | $-\overset{\overset{O}{\|}}{C}CH_3$ |
| 2.58–1.00 δ | multiplets | 20H | remaining protons |

EXAMPLE VIII

To a mechanically stirred solution of 3.37 ml. (41.7 mmoles) of pyridine in 50 ml. of methylene chloride cooled to 10° to 15° under nitrogen was added portionwise over a period of 30 minutes 1.89 g. (18.9 mmoles) of chromium trioxide. The dark burgundy solution was then let warm to room temperature then was cooled to 0°. To the cold solution was added a solution of 0.947 g. (2.37 mmole) of the crude alcohol prepared in Example VII in 7.0 ml. of methylene chloride with the concomitant formation of a dense black precipitate. The suspension was stirred in the cold for 15 minutes then 7.21 g. (52.2 mmoles) of finely ground sodium bisulfate monohydrate was added. After being stirred for 10 minutes 6.25 g. (52.2 mmoles) of anhydrous magnesium sulfate was added. After being stirred for 5 minutes the dark suspension was filtered through a pad of Celite, was washed with methylene chloride, then was concentrated by rotary evaporation (bath <10°) to afford the crude, dark brown, oily methyl 7-[2β-formyl-3α-(tetrahydropyran-2-yloxy)-5α-acetoxycyclopent-1α-yl]heptanoate which was used without purification.

EXAMPLE IX

To a suspension of 110 mg. (2.61 mmoles) of a 57.0% dispersion of sodium hydride in mineral oil in 20 ml. of dimethoxyethane was added 580 mg. (2.61 mmoles) of dimethyl-2-oxoheptylphosphonate. The mixture was stirred at room temperature for 1 hour under nitrogen with the concomitant formation of a dense white precipitate. To this suspension was added a solution of 0.947 g. (2.37 mmoles) of the crude aldehyde prepared in Example VIII in 4 ml. of dimethoxyethane. The resultant slightly turbid, brown solution was stirred at room temperature for 2.0 hours under nitrogen. The reaction was then quenched by the addition of glacial acid to pH ~ 7 and was concentrated by rotary evaporation. The resultant brown semisolid was slurried with benzene, filtered, and concentrated by rotary evaporation to afford the crude product weighing 1.27 g. The crude product was purified by column chromatography on silica gel (Baker Reagent "Analyzed" 60-200 mesh) using methylene chloride then a 1:1 mixture of methylene chloride:ethyl acetate as eluent. After elution of less polar impurities, the oily product, methyl 9α-acetoxy-11α-(tetrahydropyran-2-yloxy)-15-oxo-trans-13-prostenoate weighing 0.970 mg. (83.0% yield) was collected.

Spectra:
ir (CHCl$_3$):
1740 cm$^{-1}$ ester carbonyls
1670 and 1640 cm$^{-1}$ enone carbonyl
nmr (CDCl$_3$):

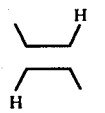

| 6.97–5.93 δ | multiplet | 2H | |
| 5.25–4.95 δ | multiplet | 1H | —CH—OAc |
| 4.44–4.70 δ | multiplet | 1H | —O—CH—O— |
| 3.66 δ | singlet | 3H | —O—CH$_3$ |
| 4.32-3.18 δ | multiplet | 5H | —OCH— & —O—CH$_2$— |
| 2.06 δ | singlet | 3H | $-\overset{\overset{O}{\|}}{C}CH_3$ |
| 2.88–0.70 δ | multiplets | 32H | remaining protons |

EXAMPLE X

To a solution of 1.07 g. (2.17 mmoles) of the enone prepared in Example IX in 6.5 ml. of dimethoxyethane was added dropwise 2.17 ml. (1.08 mmoles) of a 0.5M Zn(BH$_4$)$_2$ solution in dimethoxyethane. After being stirred at room temperature under nitrogen for 3 hours the reaction was quenched by the dropwise addition of a saturated aqueous solution of sodium bitartrate until gas evolution ceased. The quenched heterogeneous solution was stirred at room temperature for 5 minutes, was diluted with methylene chloride, was dried (anhydrous magnesium sulfate), and was concentrated to afford methyl 9α-acetoxy-11α-(tetrahydropyran-2-yloxy)-15-hydroxy-trans-13-prostenoate as a colorless, viscous oil weighing 1.07 g. (100% yield).

Spectra:
ir (CHCl$_3$):
1740 cm$^{-1}$ ester carbonyls
nmr (CDCl$_3$):

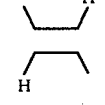

| 5.48–5.75 δ | multiplet | 2H | |
| 5.02–5.32 δ | multiplet | 1H | CH—OAc |
| 4.53–4.83 δ | multiplet | 1H | O—CH—O |
| 3.70 δ | singlet | 3H | —O—CH$_3$ |
| 3.27–4.31 δ | multiplets | 5H | —O—CH— & —O—CH$_2$— |
| 2.06 δ | singlet | 3H | $-\overset{\overset{O}{\|}}{C}CH_3$ |
| 0.68–2.84 δ | multiplets | 34H | remaining protons |

The product of this example may be treated by the process of Example XIV to yield 9α-15α-dihydroxy-11α-(tetrahydropyran-2-yloxy)-trans-13-prostenoic acid.

EXAMPLE XI

A solution of 1.07 g. (2.16 mmoles) of the crude THP ether prepared in Example X in 10.7 ml. of a 65:35 mixture of acetic acid:water was stirred at 40° ± 2° under nitrogen for 2.5 hours. The reaction mixture was then concentrated to afford the crude epimeric diol mixture as a slightly yellow oil weighing 1.0 g. The crude oily product was purified by column chromatography on silica gel (50 g. of Baker "Analyzed"60-200 mesh) using a 4:1 mixture of ether:cyclohexane as eluent (30 ml. fractions). After removal of higher R$_f$ impurities (fraction 1-12), concentration of fractions 13–69 afforded the undesired methyl-9α-acetoxy-11α,15β-dihydroxy-trans-13-prostenoate as a viscous colorless oil weighing 0.218 g. (24.5% yield). Elution of the column with ethyl acetate afforded upon concentration of fractions 70–84 the desired methyl 9α-acetoxy-11α,15α-dihydroxy-trans-13-prostenoate as a viscous colorless oil weighing 0.277 g. (31.2% yield).

Spectra:
ir (CHCl$_3$):
1620 cm$^{-1}$ ester carbonyls
970 cm$^{-1}$ trans double bond
nmr (CDCl$_3$):

| 5.72–5.49 δ | multiplet | 2H | |
|---|---|---|---|
| 5.33–5.00 δ | multiplet | 1H | —CH—OAc |
| 4.32–3.66 δ | multiplets | 4H | —CHOH |
| 3.66 δ | singlet | 3H | —O—CH₃ |
| 2.05 δ | singlet | 3H | $\begin{array}{c}\text{O}\\\|\\-\text{OCCH}_3\end{array}$ |
| 2.87–0.68 δ | multiplets | 27H | remaining protons |

EXAMPLE XII

A mixture of 60 mg. (0.15 mmoles) of the diol prepared in Example XI, 0.45 ml. (0.45 mmole) of 1.0 N aqueous sodium hydroxide, 0.45 ml. of tetrahydrofuran, and 0.45 ml. of absolute methanol was stirred under nitrogen at room temperature for 1.5 hours. The solution was then acidified by the addition of 0.45 ml. of 1.0 N aqueous hydrochloric acid (pH of acidified solution was ca. 5). The acidified solution was extracted with ethyl acetate (4 × 2 ml.). The combined extracts were dried (anhydrous magnesium sulfate) and concentrated to afford the white, solid prostaglandin $F_{1\alpha}$ weighing 55 mg. (103% yield). Crystallization of the solid from ethyl acetate:cyclohexane afforded white microcrystals which melted at 98°–100.5° C. alone and when admixed with authentic $PGF_{1\alpha}$.

EXAMPLE XIII

A mixture of 0.210 g. (0.510 mmole) of the chromatographed diol of Example XI, 0.14 ml. (1.53 mmoles) of dihydropyran, 4.2 ml. of methylene chloride, and 1 crystal of p-toluenesulfonic acid monohydrate was stirred at room temperature under nitrogen for 20 minutes. The reaction mixture was then diluted with ether, was washed with saturated aqueous sodium bicarbonate, was dried (anhydrous magnesium sulfate), and was concentrated to give the oily methyl 9α-acetoxy-11α,15α-bis-(tetrahydropyran-2-yloxy)-trans-13-prostenoate weighing 0.320 g. (105% yield).

Spectra:
ir (CHCl₃):
  1725 cm⁻¹  ester carbonyls
  970 cm⁻¹  trans double bond
nmr (CDCl₃):

| 5.74–5.32 δ | multiplet | 2H | $\begin{array}{c}\text{H}\\\diagdown\diagup\\\diagup\diagdown\\\text{H}\end{array}$ |
|---|---|---|---|
| 5.32–4.88 δ | multiplet | 1H | —CHOAc |
| 4.88–4.52 δ | multiplet | 2H | O—CH—O |
| 4.30–3.20 δ | multiplet | 1OH | —O—CH₂— & O—CH— |
| 3.67 δ | singlet | 3H | —OCH₃ |
| 2.04 δ | singlet | 3H | $\begin{array}{c}\text{O}\\\|\\-\text{OCCH}_3\end{array}$ |
| 2.83–0.78 δ | multiplets | 35H | remaining protons |

EXAMPLE XIV

A homogeneous solution of 0.253 g. (0.436 mmole) of the crude bis-THP ester prepared in Example XIII, 1.3 ml. (1.30 mmoles) of a 1.0N aqueous sodium hydroxide solution, 1.3 ml. of methanol, and 1.3 ml. of tetrahydrofuran was stirred under nitrogen overnight. The reaction was then quenched by the addition of 1.30 ml. (1.30 mmoles) of a 1.0N aqueous hydrochloric acid solution. The quenched solution was diluted with ethyl acetate. The organic layer was dried (anhydrous magnesium sulfate) and concentrated to afford the colorless, oily product. The crude product was purified by column chromatography on Baker "Analyzed" silica gel (60–200 mesh) using first chloroform as eluent to remove high $R_f$ impurities. Elution with ethyl acetate afforded the colorless, oily 9α-hydroxy-11α,15α-bis-(tetrahydropyran-2-yloxy)-trans-13-prostenoic acid weighing 0.194 g. (84.8% yield). The nmr and ir spectra of the chromatographed product were superimposable on those of the known compound.

EXAMPLE XV

To a solution, cooled under nitrogen to −15° to −20°, of 0.194 (0.371 mmole) of the chromatographed acid prepared in Example XIV in 4.0 ml. of acetone was added dropwise 0.163 ml. (0.408 mmole) of Jones' reagent. The reaction was stirred in the cold for 15 minutes then was quenched by the addition of 0.194 ml. of isopropanol. The quenched reaction was stirred in the cold for 5 minutes then was diluted with ethyl acetate. The organic solution was washed with water (2×) and saturated brine (1×), was dried (anhydrous magnesium sulfate), and was concentrated to afford the colorless, oily 9-oxo-11α,15α-bis-(tetrahydropyran-2-yloxy)-13-trans-prostenoic acid weighing 0.171 g. (88.3% yield).

EXAMPLE XVI

A homogeneous solution of 0.171 g. (0.328 mmole) of the crude THP ether of Example XV in 2 ml. of a 65:35 mixture of acetic acid:water was stirred under nitrogen at 40° ± 2° for 5 hours. The reaction was concentrated by rotary evaporation followed by oil pump. The crude, oily product was purified by column chromatography on silica gel (Mallinckrodt CC-4). Elution with chloroform removed high $R_f$ impurities. Elution with ethyl acetate afford the white, solid PGE₁ weighing 84 mg. (72.5% yield). The white solid melted without depression when admixed with a previously prepared sample of PGE₁ at 113.5°–114°.

If PGA₁ is desired, the PGE₁ is treated with 97% formic acid for 2½ hours. The resulting mixture is diluted with ice water and the aqueous mixture is extracted three times with ethyl acetate. This extract is dried (Na₂SO₄) and concentrated (aspirator pressure, ca. 40°–50°) to give a crude oil. Chromatography of the crude product is performed on acidic silica gel using mixtures of chloroform and methanol as the eluent.

EXAMPLE XVII

Examples I–XVI are repeated substituting an appropriate amount of dimethylisopropylsilyl chloride for the dihydropyran introduced in Example I and Example XII, substituting diazooctane for the diazomethane introduced in Example V, and substituting octanoic anhydride for the acetic anhydride introduced in Example VI.

EXAMPLE XVIII

Examples I–XVI are repeated substituting dihydrofuran for the dihydropyran introduced in Example I and Example XII, contacting the acid produced in Example IV with dicyclohexylcarbodiimide and 9-hydroxyfluorene rather than introducing diazomethane as in Example V, and substituting 9-fluorenecarboxylic acid chloride for the acetic anhydride introduced in Example VI.

What is claimed is:
1. A process for the preparation of prostaglandins of the "one"-series comprising the steps of:
  A. contacting the ylide of (4-carboxy-n-butyl)triphenyl-phosphonium bromide with a compound of the formula

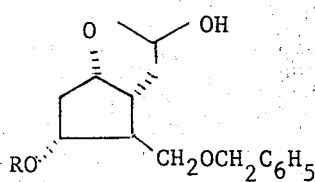

to produce a hydroxycarboxylic acid of the formula:

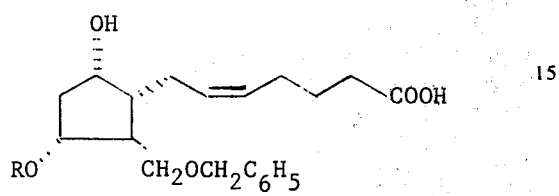

and esterifying the carboxy and acylating the hydroxy group of said hydroxycarboxylic acid;

B. catalytically hydrogenating the resulting compound of the formula:

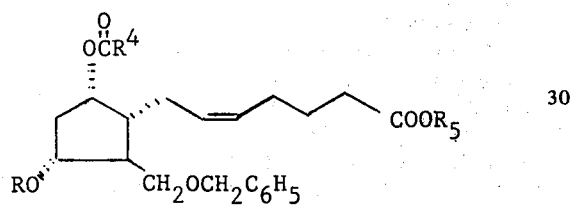

to form a saturated compound of the formula:

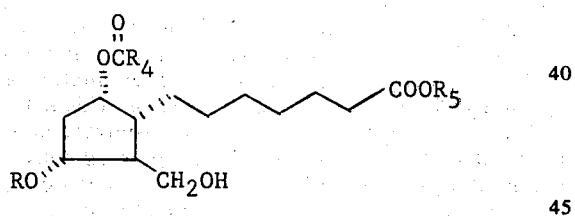

C. oxidizing said saturated compound to form an aldehyde of the formula:

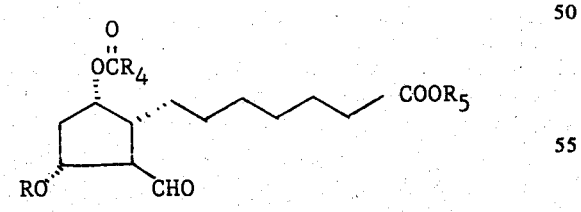

D. contacting said aldehyde with the ylide of dimethyl-2-oxoheptylphosphonate to form a compound of the formula:

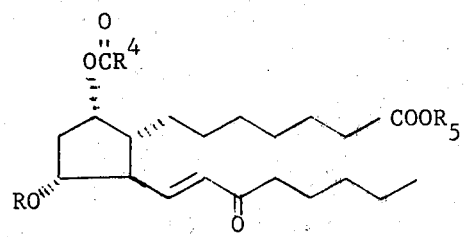

E. reducing said compound of Step D to form a compound of the formula:

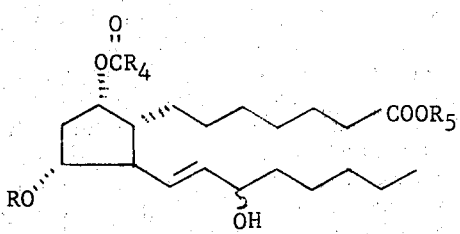

F. hydrolyzing with acid said compound of Step E to form, after chromatographic purification, compounds of the formula:

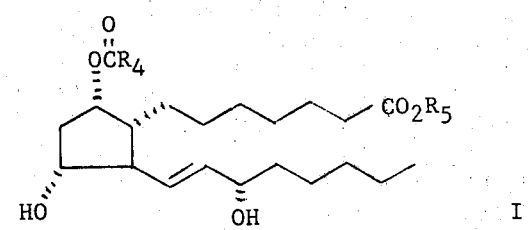

and

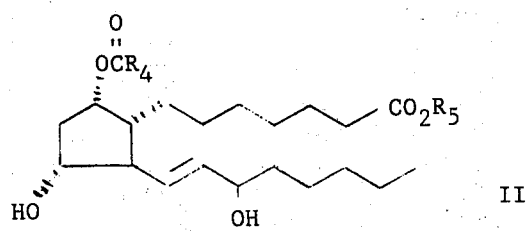

and

G. converting Compound I of Step F to a prostaglandin of the "one"-series.

2. The process of claim 1 in which R is tetrahydropyranyl and $R_4$ and $R_5$ are each methyl.

* * * * *

UNITED STATES PATENT AND TRADEMARK OFFICE
CERTIFICATE OF CORRECTION

PATENT NO. : 3,992,439
DATED : November 16, 1976
INVENTOR(S) : Thomas K. Schaaf and Elias J. Corey It is certified that error appears in the above-identified patent and that said Letters Patent are hereby corrected as shown below:

Col. 20, line 58, "din of the 'one'-series." should read -- din of the "one"-series, R being tetrahydropyranyl, tetrahydrofuranyl or dimethylisopropylsilyl and each of $R_4$ and $R_5$ being alkyl having 1 to 8 carbon atoms, phenylalkyl having 1 to 3 carbon atoms in the alkyl moiety, phenyl, tolyl, biphenyl or fluorenyl. --

Signed and Sealed this

Twenty-second Day of March 1977

[SEAL]

Attest:

RUTH C. MASON
Attesting Officer

C. MARSHALL DANN
Commissioner of Patents and Trademarks